US006916796B2

United States Patent
Wolf

(10) Patent No.: US 6,916,796 B2
(45) Date of Patent: Jul. 12, 2005

(54) USE OF PULLULAN AS A SLOWLY DIGESTED CARBOHYDRATE

(75) Inventor: Bryan W. Wolf, Johnstown, OH (US)

(73) Assignee: Abbott Laboratories, Abbott Park, IL (US)

( * ) Notice: Subject to any disclaimer, the term of this patent is extended or adjusted under 35 U.S.C. 154(b) by 175 days.

(21) Appl. No.: 10/167,912

(22) Filed: Jun. 12, 2002

(65) Prior Publication Data

US 2003/0232067 A1 Dec. 18, 2003

(51) Int. Cl.$^7$ ............................................. A61K 31/719
(52) U.S. Cl. ..................... 514/54; 536/123.12; 426/658
(58) Field of Search ...................... 514/54; 536/123.12; 426/658

(56) References Cited

U.S. PATENT DOCUMENTS

| | | | | |
|---|---|---|---|---|
| 3,875,308 A | * | 4/1975 | Kato et al. ................... | 426/549 |
| 4,629,725 A | | 12/1986 | Hiji ............................. | 514/60 |
| 4,913,925 A | * | 4/1990 | Hiji ............................. | 426/599 |
| 5,116,820 A | | 5/1992 | Hiji ............................. | 514/25 |

FOREIGN PATENT DOCUMENTS

EP     0 382 355 B1     8/1997

OTHER PUBLICATIONS

Safety Studies of a Novel Starch, Pullulan: Chronic Toxicity in Rats and Bacterial Mutagenicity, T. Kimoto; 1997 Elsevier Science Ltd., Food an Chemical Toxicology 35 (1997) 323–329.

Effects of Chemical Modification on in Vitro Rate and Extent of Food Starch Digestion: An Attempt To Discover a Slowly Digested Starch, Wolf et al; Journal of Agricultural and Food Chemistry vol. 47, No. 10 pp. 4178–4183 (1999).

Energy Value of a Mixed Glycosidic Linked Dextrin Determined in Rats, Tsuji et al; Journal of Agricultural and Food Chemistry vol. 46 No. 6 2253–2259 (1998).

* cited by examiner

*Primary Examiner*—James O. Wilson
*Assistant Examiner*—Leigh C. Maier
(74) *Attorney, Agent, or Firm*—Nickki L. Parlet

(57) ABSTRACT

The present invention is directed to the use of pullulan as a slowly digested carbohydrate and to its incorporation into food products, especially beverages and meal replacement products.

18 Claims, 4 Drawing Sheets

USE OF PULLULAN AS A SLOWLY DIGESTED CARBOHYDRATE

This application is directed to the discovery of a new slowly digested carbohydrate, pullulan, and to its use in the dietary management of diabetics and to food products containing pullulan.

BACKGROUND

Primary treatment for glucose intolerance is strict adherence to a diet that minimizes postprandial glucose response, and in many cases, use of medications (insulin or oral hypoglycemic agents).

Before 1921, starvation was the only recognized treatment of diabetes mellitus (DM). Since the discovery of exogenous insulin, diet has been a major focus of therapy. Recommendations for the distribution of calories from carbohydrate and fat have shifted over the last 75 years. Based on the opinions of the time, the best mix to promote metabolic control are listed in Table 1 below.

TABLE 1

History of Recommended Caloric Distribution of Persons with DM

| Year | Carbohydrate (%) | Protein (%) | Fat (%) |
|---|---|---|---|
| 1921 | 20 | 10 | 70 |
| 1950 | 40 | 20 | 40 |
| 1971 | 45 | 20 | 35 |
| 1986 | 50–60 | 12–20 | 30 |
| 1994 | * | 10–20 | * |

* based on nutritional assessment
^ <10% saturated fat

Early recommendations limited dietary carbohydrate, because glycemic control was generally better with this type of regimen. However, over the years researchers found that low-carbohydrate, highfat diets were associated with dyslipidemias and cardiovascular disease. In 1950, the American Diabetes Assodation (ADA) recommended increasing the proportion of calories provided by carbohydrate to lower cardiovascular risk. As the medical community gained a greater understanding of diabetes, dietary recommendations continued to evolve by suggesting increased consumption of carbohydrates.

Part of this evolution stemmed from the discovery that not all carbohydrates produce an equivalent glycemic response. Simple sugars, such as glucose, are rapidly absorbed by a human and produce an immediate spike in the blood glucose levels of a diabetic. More complex carbohydrates, such as starches, do not produce such an immediate spike. Complex carbohydrates are not directly absorbed. They are enzymatically converted to glucose, and other simple sugars, during the process of digestion. Thus, complex carbohydrates produce a blunted glycemic response in diabetics, because they are gradually converted to glucose and absorbed at a reduced rate.

Other complex carbohydrates, such as fibers, are considered indigestible. These indigestible carbohydrates are typically polymeric polysaccharides. They contain glycosidic linkages that human enzymes are incapable of cleaving. Thus, while the polysaccharides produce a sense of fullness in the patient, they are not digested and do not ultimately lead to an absorption of glucose.

Tsuji et al demonstrated what impact an indigestible polysaccharide had no blood glucose levels in a rat model at J. Agric Food Chem 1998, 46,2253. Tsuji found that the oral administration of glucose produced significant rise (about a five fold increase) in blood glucose levels after 30 min. By contrast, the indigestible polysaccharide, Fibersol, produced essentially no change in the animals blood glucose levels after 30 min.

Thus, the phrase "indigestible polysaccharide" is a term of art to food and nutritional scientists. It is used to describe a carbohydrate that a human's digestive enzymes are incapable of converting to glucose, or other simple sugars. A number of indigestible polysacharides have been described in the literature. These include pectins, celluloses, plant gums (e.g. guar gum), hemicellulose, polydextrose, xanthan gum, inulin, plant exudates, algal polysarcharides, modified celluloses, modified staches (e.g. Fibersol 2), etc.

Another indigestible carbohydrate is available from Hayashibara Co., Ltd., of Okayama, Japan and is referred to as pullulan. Hayashibara reports that pullulan is an edible plastic having adhesive properties. It reports that pullulan is safe for use as a food ingredient. It has been used as a texturizer in seasonings, dressings, and meat products. Hayashibara also recommends using pullulan as an edible ink.

Hayashibara has evaluated the digestibility of pullulan. It reports that pullulan is indigestible, like cellulose or pectin. The data in Table 2 was reproduced from a Hayashibara sales aid. It describes the effects of digestive enzymes on pullulan.

TABLE 2

The effects of different enzymes on Pullulan as reported by the manufacturer Hayashibara Co. Ltd.

| | | Specimen 1* | | Specimen 2* | |
|---|---|---|---|---|---|
| Enzymatic Source | pH | 3 hrs | 22 hrs | 3 hrs | 22 hrs |
| Porcine small intestine | 6.8 | 0 | 0.72 | 0.088 | 0.51 |
| Pancreas | 5.0 | 0.46 | 0.90 | 1.52 | — |
| Saliva | 6.0 | 0.48 | 2.33 | 0.48 | 2.5 |
| Porcine liver | 6.8 | 0.72 | — | 0.72 | — |

*Formation of reducing sugars (in mg) per 20 mg of Pullulan (i.e. breakdown of bonds between the glucose subunits of pullulan).

Other entities besides Hayshibara have also evaluated the properties of pullulan. The readers attention is directed to U.S. Pat. Nos. 5,116,820 and 4,629,725. Hiji reports that pullulan inhibits the absorption of sucrose. Thus, it can be added to foods designed for diabetics at levels of from 0.25% to 5%, based upon the total weight of the carbohydrate present in the food. Hiji also reports that the co-administration of gymnemic acid enhances the anti-absorptive properties of the pullulan.

Kimoto et al reported the results of an animal safety trial carried out with pullulan. Food and Chemical Toxicology 23, (1997) 323–329. Kimoto also reports that pullulan is an indigestible polysaccharide. On page 324, Kimoto et al reports that minimal glucose was generated by pullulan when exposed to enzymes.

Thus a fair reading of the prior art is that pullulan is reported to be an indigestible potysaccharide. This means that humans will not convert pullulan to glucose and the ingestion of pullulan will not increase serum glucose levels. Thus, while the literature teaches that pullulan may have efficacy as a fiber, it would not motivate one to use pullulan as slowly digested carbohydrate. The prior art teaches that such a use would be futile because humans are incapable of converting pullulan to glucose or other simple sugars.

SUMMARY OF THE INVENTION

In accordance with the present invention it has been discovered that the literature has mischaracterized pullulan.

Pullulan is not an indigestible carbohydrate. In fact, it has been discovered that pullulan is a slowly digested carbohydrate. This means that human enzymes gradually convert pullulan to glucose. The gradual conversion of pullulan to glucose will result in a gradual rise in blood glucose levels in a human.

The discovery of this mischaracterization means that applicants have discovered a number of new uses for pullulan. As a slowly digested carbohydrate, substantial quantities of the pullulan may be incorporated into foods designed for diabetics, thereby providing a blunted glycemic response. The pullulan may be incorporated into meal replacement products, such as beverages and bars. Alternatively, the pullulan may be incorporated into dietetic snack foods designed for diabetics. The pullulan may also be used to control nighttime hypoglycemia in diabetics in need of such therapy.

Pullulan may also be used in foods designed for use in a weight loss program. The gradual release of glucose from the pullulan will produce a feeling of satiety in these individuals. Pullulan may also be used in foods and beverages designed for athletes (i.e. "sport drinks" and "sport bars"). Pullulan will also be beneficial to patients with impaired glucose tolerance. These individuals are often referred to as prediabetics or individuals at risk of developing diabetes. In summary, the pullulan may be used for any application suitable for a slowly digested carbohydrate.

DETAILED DESCRIPTION OF THE INVENTION

Figure 1:
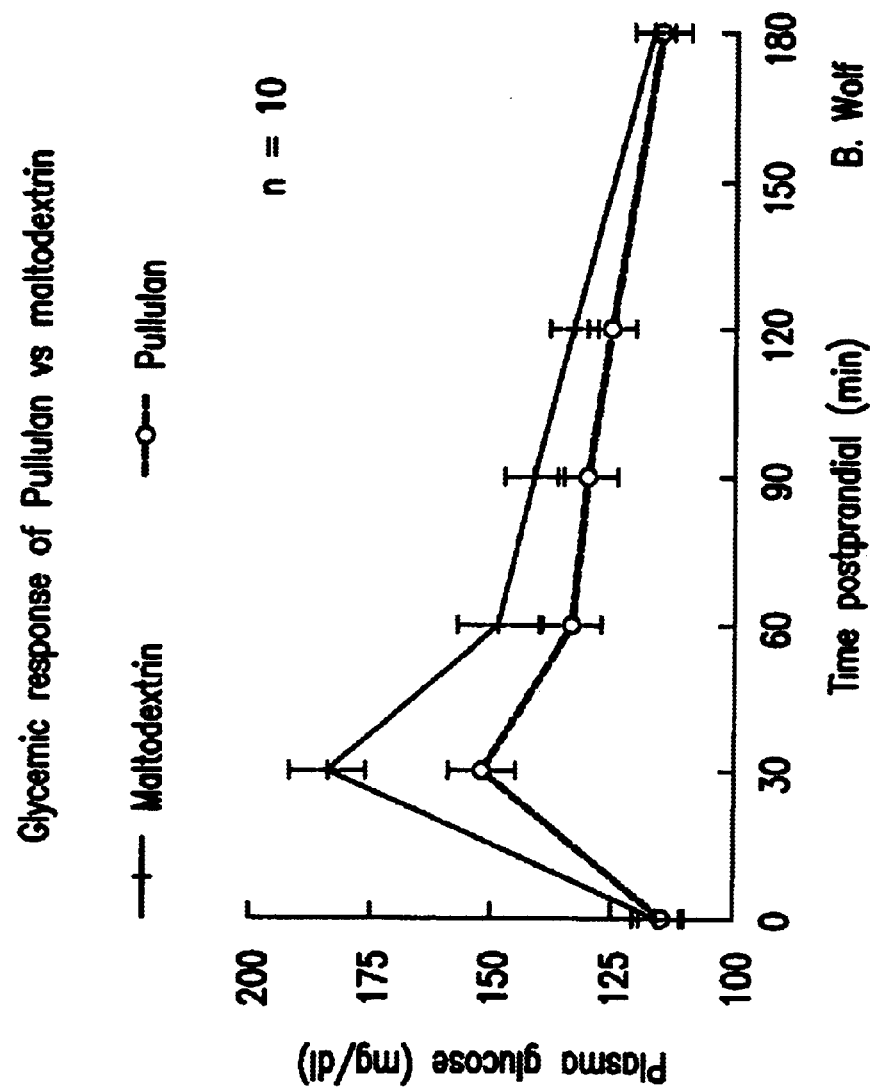
FIG. 1 presents the glycemic response of Zucker rats fed pullulan and maltodextrin as described in Example IV.

As used in this application the following terms have the meanings specified below, unless otherwise noted. The plural and the singular should be considered to have the same meanings, other than the quantity:

a) "relative glycemic response" (GI) is calculated by dividing the blood glucose incremental area under the curve (AUC) of the test food by the blood glucose incremental AUC of the reference food and multiplying by 100, where the carbohydrate content of test and reference foods are the same. The reference food is typically glucose or white bread, which has the standard GI of 100.

b) "a blunted glycemic response" refers to a reduction in the relative glycemic response when compared with an equivalent dose of glucose.

c) "hypoglycemia" refers to a decrease in the plasma glucose concentration to a level sufficient to produce symptoms, with attenuatron of symptoms upon restoration of normal glucose concentration.

d) "DM" refers to diabetes mellitus and is described in detail in Joslin's Diabetes Mellitus. Kahn and Weir (eds.) 1994 e) "indigestible carbohydrate" refers to a carbohydrate that is resistant to endogenous digestion in the human upper digestive tract, or any non-ruminant animal.

f) the terms "indigestible carbohydrate", "indigestible polysaceharide", "non-digestible carbohydrate", and "non-digestible polysaccharide" should be considered as synonyms.

g) "slowly digested carbohydrate" refers to a carbohydrate that has a slow rate of digestion, in which the gold standard is raw cornstarch, and more specifically has a rate of digestion that is slower than hydrolyzed cornstarch, (for example Lodex 15® from Cerester).

h) "rapidly digested carbohydrate" refers to a carbohydrate that is rapidly digested, e.g. unmodified maltodextrin (for example Lodex 15® from Cerester) and is digested at a rate equal to or faster than an unmodified malodextrin, such as Lodex 15®.

i) The term "total calories" refers to the total caloric content of a defined weight or volume of the finished nutritional product.

j) The term "meal replacement product" and the term "nutritionals" should be considered as synonyms.

k) The term "total carbohydrate content"refers to the sum of all carbohydrate components, analytically defined as Total Solids—(Ash+Fat+Protein).

l) the term "Reference Daily Intakes or RDI" refers to a set of dietary references based on the Recommended Dietary Allowances for essential vitamins and minerals. The Recommended Dietary Allowances are a set of estimated nutrient allowances established by the National Academy of Sciences, which are updated periodically to reflect current scientific knowledge.

m) the term "patient" refers to humans, dogs, cats, and any other non-ruminant animal.

n) Any reference to a numerical range in this application should be considered as being modified by the adjective "about". Further, any numerical range should be considered to provide support for a claim directed to a subset of that range. For example, a disclosure of a range of from 1 to 10 should be considered to provide support in the specification and claims to any subset in that range (i.e., ranges of 2–9, 3–6, 4–5, 2.2–3.6, 2.1–9.9, etc.).

As noted above, the prior art has mischaracterized pullulan. The literature contains animal data documenting that pullulan is a nondigestible carbohydrate. As will be demonstrated in the experimental section of this application, this characterization is incorrect. Applicants have demonstrated, in humans, that pullulan is a slowly digested carbohydrate.

Pullulan is a water-soluble, viscous polysaccharide, an alpha-glucan, consisting of glucose units with a relatively simple linear structure, that is, units of three alpha-1,4-linked glucose molecules that are repeatedly polymerized by alpha-1,6 linkages on the terminal glucose. Typical food starches such as corn starch, consist of 27% amylose (alpha 1,4-linked glucose molecules) and 73% amylopectin, which contain both alpha 1,4- and alpha 1,6 glucose linkages. For pullulan, however, the alpha-1,6 linkage serves to cross-link individual short chains resulting in a stair step structure (structure 1). As pullulan has an average molecular weight of 50,000–500,000, n in structure 1 ranges from 300 to 3000. Kimoto et al Food and Chemical Toxicology 35 (1997) 323–329.

Structure 1

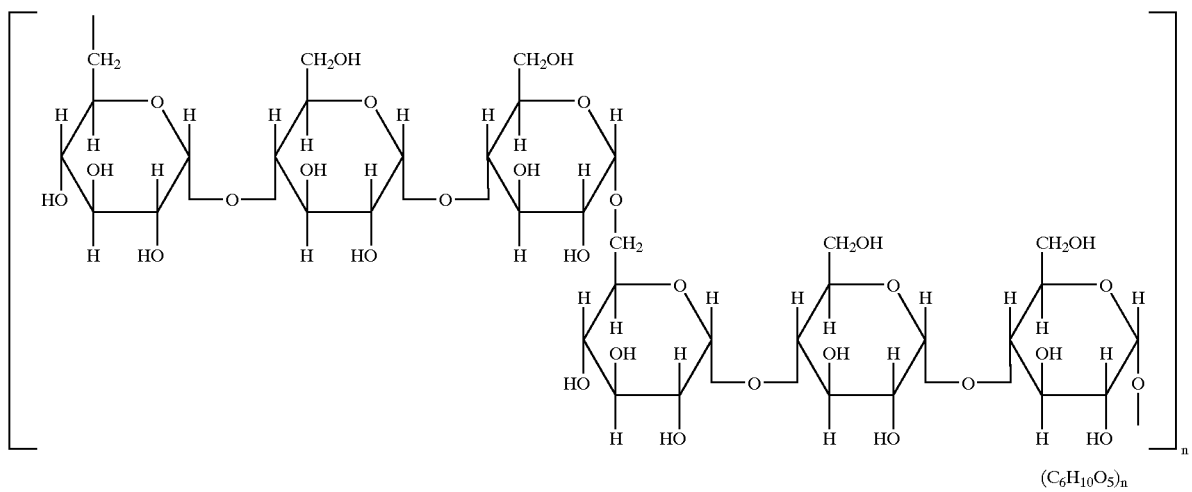

$(C_6H_{10}O_5)_n$

Pullulan is elaborated extracellularly by the black yeast, *Aureobasidiium pullulans*. It is produced by cultivating this same yeast in a medium with sufficient carbon and nitrogen sources and minerals, under aeration. The pullulan is recovered from the culture fluid by centrifugation. It is then typically fractionated with alcohol and purified as is known in the art Kimoto et al, supra. Pullulan is also available commercially from Hayashibara Co. Ltd. of Okayama, Japan.

As noted above, it has been discovered that pullulan is a slowly digested carbohydrate. This effect can be achieved with any of the pullulan molecules having the varying molecular weights described above. The pullulan may be administered as a mixture of compounds having varying molecular weights. If desired, highly purified materials of a single molecular weight may be utilized as well.

The beneficial effects that pullulan has on the blood glucose levels of a diabetic can be achieved in a number of ways. If desired, the pullulan may be administered without any carrier. The pullulan may simply be dissolved in water and consumed by the diabetic. Alternatively, the pullulan may be sprinkled on food, dissolved in coffee, etc. The total daily dose for the diabetic will vary widely, but typically a diabetic will benefit form consuming 1–150 g/day of pullulan.

In a further embodiment, the pullulan may be incorporated into pills, capsules, rapidly dissolved tablets, lozenges, etc. These pharmaceutical dosage forms are especially useful in treating, or preventing, hypoglycemia. The dose for hypoglycemia can vary widely, but will typically range from 1 to 20 g/dose and more typically 5 g/dose. Methods for preparing such dosage forms are well known in the art. The readers attention is directed to the most recent edition of Remingtons Pharmaceutical Sciences for guidance on how to prepare such dosage forms.

While the pullulan may be administered as a single entity, it will typically be incorporated into food products and consumed by the diabetic during their meals or snack. If desired, the diabetic may simply modify the recipe of foods they normally consume. They may simply replace glucose, and other rapidly digested carbohydrates, with an equivalent amount of pullulan. Replacing the rapidly digested sugars with pullulan will significantly reduce the glycemic index of the food. A similar strategy may be utilized by individuals attempting to lose weight because the pullulan will provide for an extended release of glucose and delay the individuals desire to consume additional calories.

While such a strategy will produce foods with a blunted glycemic response, it will also produce a relatively bland diet that many individuals will find objectionable because pullulan is tasteless. Therefore, in a further embodiment, the pullulan will be incorporated into beverages, bars, cookies, etc. that have been specifically designed to enhance the palatability of the pullulan and thereby enhance patient/consumer acceptance.

Typically, the pullulan will be incorporated into meal replacement beverages such as Glucerna®, Ensure®, Choice DM®, Slim Fast®, Pediasure®, Glytrol®, Resource®, Diabetic, etc. The pullulan may also be incorporated into meal replacement bars such as PowerBar®, Glucerna® bars, Choice DM® bars, Ensure® bars, and Boost® bars, etc. Alternatively, the pullulan maybe incorporated into juices, carbonated beverages, bottled water, etc. Methods for producing any of such food products or beverages are well known to those skilled in the art. The following discussion is intended to illustrate such diabetic and weight loss meal replacement products and their preparation.

Most meal replacement products (i.e., bars or liquids) provide calories from fat, carbohydrates, and protein. These products also typically contain vitamins and minerals, because they are intended to be suitable for use as the sole source of nutrition. While these meal replacement products may serve as the sole source of nutrition, they typically don't. Individuals consume these products to replace one or two meals a day, or to provide a healthy snack. The nutritional products of this invention should be construed to to include any of these embodiments.

The amount of these nutritional ingredients can vary widely depending upon the targeted patient population (i.e., diabetics vs. non-diabetics, organoleptic considerations, cultural preferences, use, etc.). As a general nonlimiting guideline however, the meal replacement products of this invention will contain the following relative amounts of protein, fat, and carbohydrate (based upon the relative percentage of total calories):

TABLE 3

Nutritional Formula Component Ranges

| Component | Preferred range (% Calories) | More preferred range (% Calories) |
| --- | --- | --- |
| Protein source | 0–35 | 15–25 |
| Fat source | <55 | 10–40 |
| Carbohydrate system* | 25–100 | 25–55 |

*including pullulan

The novelty of these meal replacement products is the use of pullulan to provide a significant source of carbohydrate calories. As noted above, the carbohydrate will provide from about 25–100% of total calories. Sufficient pullulan should be incorporated into the product so that the pullulan will comprise at least 5 w/w % of the carbohydrate system (when measured on a dry weight basis, i.e. not dissolved in a liquid). More typically, the pulfulan will comprise from about 5 to about 100 w/w% of the carbohydrate system. Alternatively, the pullulan should provide at least 5% of total carbohydrate calories and more typically from 10 to 50%.

The remaining portion of the carbohydrate system (i.e., one or more carbohydrates including pullulan) may be provided by any carbohydrate system suitable for humans, taking into account any relevant dietary restrictions (i.e., if intended for a diabetic). Examples of suitable carbohydrates that may be utilized include starch, modified starch, hydrolyzed corn starch, maltodextrin, glucose polymers, sucrose, corn syrup solids, glucose, fructose, lactose, high fructose corn syrup, fructooligosaccharides, honey, dietary fiber, sugar alcohols (e.g., maltitol).

Specialized carbohydrate blends have been designed for diabetics to help moderate their blood glucose levels. Examples of such carbohydrate blends are described in U.S. Pat. No. 4,921,877 to Cashmere et al., U.S. Pat. No. 5,776,887 to Wibert et al., U.S. Pat. No. 5,292,723 to Audry et al. and U.S. Pat. No. 5,470,839 to Laughlin et al, the contents of which are all incorporated by reference. Any of these carbohydrate blends may be utilized in association with pullulan to further reduce the glycemic index of the product.

If desired, nonabsorbent carbohydrates may be incorporated into the carbohydrate system as well. These nonabsorbent carbohydrate will comprises less than or equal to about 20 wt/wt % of the carbohydrate system, and more typically less than or equal to about 15 wt/wt % of the carbohydrate system. The term "nonabsorbent carbohydrates" refers to a carbohydrate moiety with a degree of polymerization greater than about 20 and/or a molecular weight greater than about 3,600, that is resistant to endogenous digestion in the human upper digestive tract. Nonabsorbent carbohydrates possess many of the characteristics of total dietary fiber. However, they are not quantifiable by the AACC Method 32-07 for fiber and consequently they are not included in total dietary fiber values of the instant invention. Examples of nonabsorbent carbohydrates sources of the instant invention typically include chemically modified starches such as Fibersol, polydextrose and inulin.

Typically, the carbohydrate system will also contain dietary fiber. The quantity of dietary fiber can vary significantly but will typically range from 3 to 20 w/w % of the carbohydrate system (on a dry weight basis). Dietary fiber, as used herein and in the claims, is understood to be all of the components of a food that are not broken down by endogenous enzymes in the human digestive tract to small molecules that are absorbed into the bloodstream. These food components are mostly celluloses, hemicelluloses, pectin, gums, mucilages, and lignins. Fibers differ significantly in their chemical composition and physical structure and therefore their physiological functions.

The properties of fibers (or fiber systems) that impact on physiological function are solubility and fermentability. With regard to solubility, fiber can be divided into soluble and insoluble types based on the fiber's capacity to be solubilized in a buffer solution at a defined pH. Fiber sources differ in the amount of soluble and insoluble fiber they contain. As used herein and in the claims "soluble" and "insoluble" dietary fiber is determined using American Association of Cereal Chemists (AACC) Method 32-07. As used herein and in the claims, "total dietary fiber" or "dietary fiber" is understood to be the sum of the soluble and insoluble fibers determined by AACC Method 32-07 and wherein by weight at least of the fiber source comprises dietary fiber. As used herein and in the claims a "soluble" dietary fiber source is a fiber source in which at least 60% of the dietary fiber is soluble dietary fiber as determined by AACC Method 32-07, and an "insoluble" dietary fiber source is a fiber source in which at least 60% of the total dietary fiber is insoluble dietary fiber as determined by AACC Method 32-07.

Representative of soluble dietary fiber sources are gum arabic, sodium carboxymethyl cellulose, guar gum, citrus pectin, low and high methoxy pectin, oat and barley glucans, carrageenan and psyllium. Numerous commercial sources of soluble dietary fibers are available. For example, gum arabic, carboxymethyl cellulose, guar gum, pectin and the low and high methoxy pectins are available from TIC Gums, Inc. of Belcamp, Md. The oat and barley glucans are available from Mountain Lake Specialty ingredients, Inc. of Omaha, Nebr. Psyllium is available from the Meer Corporation of North Bergen, N.J. while the camageenan is available from FMC Corporation of Philadelphia, Pa.

Representative of the insoluble dietary fibers are oat hull fiber, pea hull fiber, soy hull fiber, soy cotyledon fiber, sugar beet fiber, cellulose and corn bran. Numerous sources for the insoluble dietary fibers are also available. For example, the corn bran is available from Quaker Oats of Chicago, Ill.; oat hull fiber from Canadian Harvest of Cambridge, Minn.; pea hull fiber from Woodstone Foods of Winnipeg, Canada; soy hull fiber and oat hull fiber from The Fibrad Group of LaVale, Md.; soy cotyledon fiber from Protein Technologies International of St. Louis, Mo.; sugar beet fiber from Delta Fiber Foods of Minneapolis, Minn. and cellulose from the James River Corp. of Saddle Brook, N.J.

A more detailed discussion of fibers and their incorporation into formula may be found in U.S. Pat. No. 5,085,883 issued to Garleb et al, which is hereby incorporated by reference.

In addition to fiber, the nutritionals may also contain indigestible oligosaccharides such as fructooligosaccarieds (FOS). Indigestible oligosaccharides are rapidly and extensively fermented to short chain fatty acids by anaerobic microorganisms that inhabit the large bowel. These oligosaccharides are preferential energy sources for most Bifidobacterium species, but are not utilized by potentially pathogenic organisms such as Clostridium perfingens, C. difficile, or E. coli. The term "indigestible oligosaccharide" refers to a small carbohydrate moiety with a degree of polymerization less than or equal to about 20 and/or a molecular weight less than or equal to about 3,600, that is resistant to endogenous digestion in the human upper digestive tract.

The meal replacement products also typically contain a protein source. The protein source may contain intact proteins, hydrolyzed proteins, amino acids, or some combination thereof. The proteins that may be utilized in the nutritional products includes any protein suitable for human consumption. Such proteins are well known by those skilled in the art and can be readily selected when preparing such products. Examples of suitable proteins that may be utilized typically include casein, whey, milk protein, soy, pea, rice, corn, hydrolyzed protein and mixtures thereof. Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa.

The third component of the nutritional products of this invention is the fat. The fat source for the present invention may be any fat source or blend of fat sources suitable for human consumption. Typically the fat provides the desired levels of saturated, polyunsaturated and monounsaturated fatty adds. One skilled in the art can readily calculate how much of a fat source should be added to the nutritional product in order to deliver the desired levels of saturated, polyunsaturated and monounsaturated fatty acids. Examples of food grade fats are well known in the art and typically include soy oil, olive oil, marine oil, sunflower oil, high oleic sunflower oil, safflower oil, high oleic safflower oil, fractionated coconut oil, cottonseed oil, corn oil, canola oil, palm oil, palm kernel oil, flax seed oil, medium chain triglycerides (MCT) and mixtures thereof. If desired, structured lipids can be incorporated into the nutritional.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Oreg. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Angila Oils of North Humberside, United Kingdom. Sunflower and cottonseed oils are available from Cargil of Minneapolis, Minn. Safflower oil is available from California Oils Corporation of Richmond, Calif. Structured lipids are available from Stepan Oils, having offices in the United States and who can be reached at www.stepan.com.

The nutritional compositions of the invention typically contain vitamins and minerals. Vitamins and minerals are understood to be essential in the daily diet. Those skilled in the art appreciate that minimum requirements have been established for certain vitamins and minerals that are known to be necessary for normal physiological function. Practitioners also understand that appropriate additional amounts of vitamin and mineral ingredients need to be provided to nutritional compositions to compensate for some loss during processing and storage of such compositions. Additionally, the practitioner understands that certain micronutrients may have potential benefit for people with diabetes such as chromium, camitine, taurine and vitamin E and that higher dietary requirements may exist for certain micro nutrients such as ascorbic acid due to higher turnover in people with type 2 diabetes.

An example of the vitamin and mineral system for a complete nutritional product used as a sole source of nutrition typically comprises at least 100% of the RDI for the vitamins A, $B_1$, $B_2$, $B_6$, $B_{12}$, C, D, E, K, beta-carotene, Biotin, Folic Acid, Pantothenic Acid, Niacin, and Choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients minositol, carnitine and taurine in from about 350 Kcal to about 5600 Kcal.

An example of the vitamin and mineral system for a nutritional product used as a nutritional supplement typically comprises at least 25% of the RDI for the vitamins A, $B_1$, $B_2$, $B_6$, $B_{12}$, C, D, E, K, beta-carotene, Biotin, Folic Acid, Pantothenic Acid, Niacin, and Choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients minositol, camitine and taurine in a single serving or from about 50 Kcal to about 800 Kcal.

Artificial sweeteners may also be added to the nutritional product to enhance the organoleptic quality of the formula. Examples of suitable artificial sweeteners include saccharine, aspartame, acesulfame K and sucralose. The nutritional products of the present invention will also desirably include a flavoring and/or color to provide the nutritional products with an appealing appearance and an acceptable taste for oral consumption. Examples of useful flavorings typically include, for example, strawberry, peach, butter pecan, chocolate, banana, raspberry, orange, blueberry and vanilla.

The nutritional products of this invention can be manufactured using techniques well known to those skilled in the art. For liquid meal replacement products, generally speaking, an oil and fiber blend is prepared containing all oils, any emulsifier, fiber and the fat soluble vitamins. Three more slurries (carbohydrate and two protein) are prepared separately by mixing the carbohydrate and minerals together and the protein in water. The slurries are then mixed together with the oil blend. The resulting mixture is homogenized, heat processed, standardized with water soluble vitamins, flavored and the liquid terminally sterilized or dried to produce a powder. Alternatively, the homogenized formula may be kept undiluted and filled into appropriate containers as pudding or dried to form powder. The product is then packaged. Typically the package will provide directions for use by the end consumer (i.e., to be consumed by a diabetic, to assist with weight loss, etc.)

Solid nutritional compositions such as bars, cookies, etc. may also be manufactured utilizing techniques known to those skilled in the art. For example, they may be manufactured using cold extrusion technology as is known in the art. To prepare such compositions, typically all of the powdered components will be dry blended together. Such constituents typically. include the proteins, vitamin premixes, certain carbohydrates, etc. The fat soluble components are then blended together and mixed with the powdered premix above. Finally any liquid components are then mixed into the composition, forming a plastic like composition or dough.

The process above is intended to give a plastic mass which can then be shaped, without further physical or chemical changes occurring, by the procedure known as cold forming or extrusion. In this process, the plastic mass is forced at relatively low pressure through a die, which confers the desired shape. The resultant exudate is then cut off at an appropriate position to give products of the desired weight. If desired the solid product is then coated, to enhance palatability, and packaged for distribution. Typically the package will provide directions for use by the end consumer (i.e., to be consumed by a diabetic, to assist with weight loss, etc.)

The solid nutritionals of the instant invention may also be manufactured through a baked application or heated extrusion to produce cereals, cookies, and crackers. One knowledgeable in the arts would be able to select one of the many manufacturing processes available to produce the desired final product.

As noted above, the pullulan may also be incorporated into juices, non-carbonated beverages, carbonated beverages, flavored waters (hereinafter collectively "beverage"), etc. The pullulan will typically comprise from 10 to 100% of the total carbohydrate contact of the beverages. Methods for producing such beverages are well known in the art. The reader's attention is directed to U.S. Pat. Nos. 6,176,980 and 5,792,502, the contents of each which are hereby incorporated by reference. For example, all of the carbohydrates, including the pullulan are dissolved in an appropriate volume of water. Flavors, colors, vitamins, etc. are then optionally added. The mixture is then pasteurized, packaged and stored until shipment.

The embodiments of the present invention may, of course, be carried out in other ways than those set forth herein without departing from the spirit and scope of the invention. The present embodiments are, therefore, to be considered in all respects as illustrative and not restrictive and that all changes and equivalents also come within the description of the present invention. The following nonlimiting Examples will further illustrate the present invention.

EXAMPLE I OF THE INVENTION

One method of screening carbohydrates for their suitability for inclusion into diabetic diets is to determine the rate at which they are digested by animal or human enzymes in an in-vitro model of digestion. This technique is well known in the art and has been described by Muir and O'Dea at American Journal of Clinical Nutritional (1992) 56:123–127 and American Journal of Clinical Nutritional (1993) 57: 540–546. This analysis was carried out initially on pullulan. One sample of pullulan was heat treated by autoclaving for 10 minutes at 15 psi and 121° C., to replicate conditions routinely used in the manufacture of foods.

The following results were obtained:

TABLE A

In Vitro digestion of pullulan*
% pullulan digested

| Ingredient | 0 hr | 0.5 hr | 1 hr | 2.5 hr | 5 hr | 15 hr |
|---|---|---|---|---|---|---|
| "raw" Pullulan | 0.0 | 24.2 | 27.6 | 42.4 | 56.5 | 90.9 |
| "cooked Pullulan | 0.1 | 31.5 | 31.8 | 44.3 | 50.5 | 86.5 |

*Percent digestible starch, expressed as a percent of ingredient weight, determined by the method of Muir and O'Dea (α-amylase and amyloglucosidase enzyme system; 1992); a 15 hour in vitro incubation has been shown to correlate with the amount of starch escaping digestion in the small intestine (Muir and O'Dea 1993).
Time 0 values represent percent free glucose in samples. All values are means of duplicate samples.

Surprisingly, we discovered that pullulan was digestible, contrary to the prior art. Similar to uncooked corn starch, pullulan exhibited a slow rate of in vitro digestion. However, pullulan maintained its slow rate of in vitro digestion after cooking, which makes cornstarch rapidly digested.

EXAMPLE II

Based upon the surprising data reported in Example I, the experiment was repeated with additional samples of pullulan of varying molecular weight. For comparative purposes, glucose was tested as well. Data for corn starch as reported in the literature is reported below.

TABLE B

In Vitro starch digestion (method described by Muir and O'Dea) of pullulan*
% starch digested (DM basis)
time of starch digestion

| Ingredient | 0 hr | 0.5 hr | 1 hr | 2.5 hr | 5 hr | 15 hr |
|---|---|---|---|---|---|---|
| Glucose | 110.8 | 101.5 | 100.3 | 100.2 | 102.4 | 103.0 |
| Glucose, C | 101.5 | 90.9 | 104.5 | 91.4 | 96.7 | 91.1 |
| PF20 | 4.9 | 13.1 | 18.0 | 39.3 | 48.0 | 93.7 |
| PF2O, C | 5.9 | 16.6 | 20.9 | 45.0 | 53.6 | 95.5 |
| Pl20 | 1.2 | 13.1 | 17.3 | 41.7 | 53.6 | 103.0 |
| Pl20, C | 1.1 | 13.5 | 19.4 | 42.6 | 54.4 | 96.0 |

*Values are means of duplicate analysis. Percent digestible starch, expressed as a percent of ingredient dry matter, determined by the methods of Muir and O'Dea (α-amylase and amyloglucosidase enzyme system; 1992; a 15 hour in vitro incubation has been shown to correlate with the amount of starch escaping digestion in the small intestine (Muir and O'Dea 1993).
Time 0 values represent percent free glucose in samples.
C = cooked.
PF2O = food grade pullulan, MW of 200,000.
Pl20 = pharmaceutical grade of pullulan. MW of 200,000.

As a control glucose was tested and produced the expected result. Different grades of pullulan acted as slowly digested carbohydrate.

EXAMPLE III

This example describes further in-vitro work done with pullulan.

TABLE C

In vitro starch digestion (method described by Muir and O'Dea) of pullulan*
% starch digested (DM basis)
time of starch digestion

| Ingredient | 0 hr | 0.5 hr | 1 hr | 2.5 hr | 5 hr | 15 hr |
|---|---|---|---|---|---|---|
| Corn starch | 0 ± 0 | 30.4 ± 0.9 | 30.1 ± 0.3 | 55.2 ± 1.8 | 62.4 ± 1.2 | 78.4 ± 0.3 |
| Glucose, C | 95 | 97.8 | 100 | 102 | 108.3 | 108 |
| PA, C | 3.0 | 30.8 | 33.8 | 34.1 | 41.4 | 70.2 |
| PB, C | 2.3 | 27.2 | 25.8 | 31.5 | 54 | 59.8 |
| PC, C | 2.3 | 17.1 | 19.4 | 21.5 | 35 | 59.2 |
| PF10, C | 14 | 24.5 | 56.4 | 61.2 | 77.4 | 91.8 |

*Historical data from Sigma's raw corn starch. Percent digestible starch, expressed as a percent of ingredient dry matter, determined by the methods of Muir and O'Dea (α-amylase and amyloglucosidase enzyme system; 1992); a 15 hour in vitro incubation has been shown to correlate with the amount of starch escaping digestion in the small intestine (Muir and O'Dea 1993).
Time 0 values represent percent free glucose in samples.
C = cooked.
Values for glucose and pullulan are means of triplicate analysis.
PA = pullulan, MW of 6,010.
PB = pullulan, MW of 13,900.
PC = pullulan. MW of 49,200.
PF10 = food grade pullulan MW of 100,000.

Different molecular weights of pullulan were all digested at a slow rate and would have efficacy in a food product.

EXAMPLE IV

The following example illustrates the ability of pullulan to function as a slowly digested carbohydrate in an animal model of Type 2 diabetes mellitus (insulin resistance).

The objective of this experiment was to compare the postprandial glycemic response of male Zucker fatty fa/fa rats fed pullulan versus maltodextrin.

Animals

Twenty male Zucker fatty fa/fa rats were obtained at five weeks of age from Harlan Sprague Dawley, Inc. (Indianapolis, Ind.). Rats were individually housed in hanging naglene cages on dry bedding (San-Chips, Harlan Teklad) and were given ad libitum access to water and rat chow (pelleted; 8640 Harlan Teklad 22/5 Rodent Diet; Harlan Teklad, Madison, Wis.). The housing facility was maintained at 19 to 23° C., 30 to 70% relative humidity, and 12 hour light-dark cycle. Rats were handled 4 to 5 times per week for 3 weeks prior to this experiment in order to acclimate them to human handling for the experiment. In addition, rats were trained to orally consume a liquid carbohydrate solution via syringe for the meal tolerance test. The animal use protocol was reviewed and approved by The Ohio State University Animal Care Committee.

Dietary Treatments

The control test was a maltodextrin (Lodex 15; Cerestar USA Inc., Hammond, Ind.) challenge at ~0.9 g/kg body weight. Lodex was made into a 25% (wt./vol.) solution with water prior to challenge (total volume 10 ml). Similarly, a 25% (wt./wt.) pullulan (Sigma, St. Louis, Mo.) solution was made (total weight 14 g). Both treatments were heated in a microwave for 30 seconds at high to completely solubilize the carbohydrate solutions 2-hours before testing.

Experimental Design

The two dietary treatments were evaluated in a parallel design (10 rats per treatment). At the time of testing, rats weighed 275±5.5 g (mean±SEM) and were 8 weeks old. After an overnight fast of 16 hours, rats underwent a meal tolerance test Rats were randomly fed one of two dietary treatments (1 ml) per os. All rats consumed the diet within a 10 minute period. Blood samples were collected at baseline and 30, 60, 90, 120, and 180 minutes postprandial for glucose analysis (Precision G; Medisense, Bedford, Mass.). Rats had free access to water throughout the experiment.

Sample Collection

Blood samples were obtained via tail vein and approximately 5 $\mu$l of blood was immediately transferred directly onto a Precision G blood glucose test strip and analyzed for blood glucose concentration. Whole blood was used, however, the Precision G instrument corrects the glucose measurement and provides the data as mg glucose/dl plasma.

Results

Figure 2:
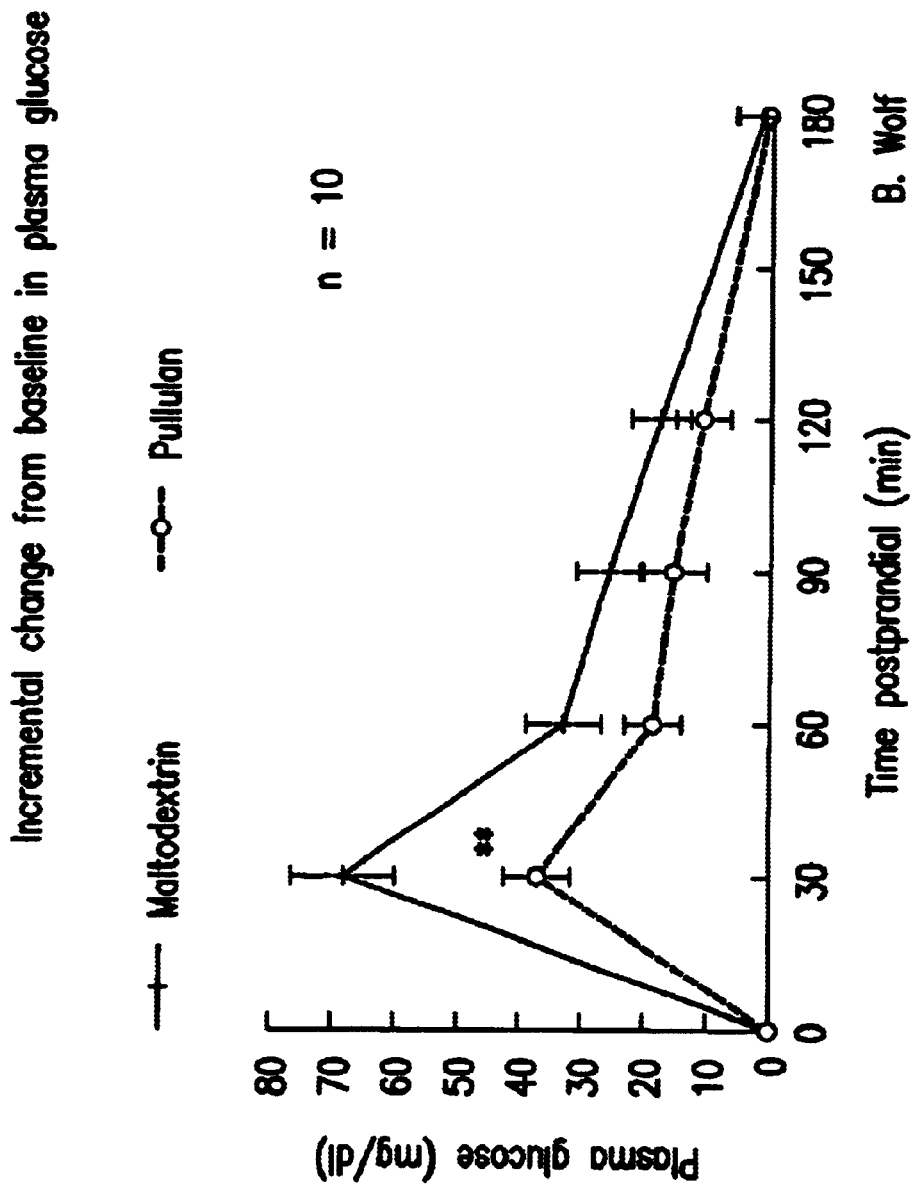
FIG. 2 presents the incremental change in blood glucose levels as described in Example IV.

The postprandial glycemic response of male Zucker fatty fa/fa rats fed maltodextrin or pullulan can be found in FIG. 1, and the incremental change from baseline in blood glucose can be found in FIG. 2. Basal blood glucose values were not different (116±5 vs. 115±5 mg/dl; maltodextrin vs. pullulan, respectively). The incremental change from baseline in blood glucose was reduced (P<0.01) by 45% for rats fed pullulan at 30 minutes postpradial (FIG. 2). Area under the curve (AUC) was calculated (Wolever and Jenkins, 1986) and was found to be lower (P<0.05) for rats fed pullulan (3 hour AUC 4812±581 vs. 2889±486, maltodextrin and pullulan, respectively).

References

Kimoto, T., Shibuya, T., Shiobara, S. Safety studies of a novel starch, pullulan: chronic toxicity in rats and bacterial mutagenicity. *Food and Chemical Toxicology* 1997, 34, 323–329.

Wolever, T. M. S., Jenkins, D. J. K The use of glycemic index in predicting the blood glucose response to mixed meals. *Am. J. Clin. Nutr.* 1986, 43, 167–172.

Wolf, B. W., L. L. Bauer, and G. C. Fahey, Jr. Effects of chemical modification on in vitro rate and extent of food starch digestion: an attempt to discover a slowly digested starch. *J. Agric. Food Chem.* 1999, 47, 4178–4183.

EXAMPLE V 1.0 Study Objectives

The primary objective was to determine the postprandial glycemic response of nondiabetic healthy adults to pullulan and maltodextrin 2.0 Investliation Protocol 2.1 Overall Study Design: Description Thirty-six healthy adult subjects who met all eligibility criteria were enrolled into the study. Twenty-eight subjects completed the protocol. The experiment followed a double-blind, two period, two treatment crossover design with a minimum of a four-day washout between treatments. Subjects returned within 14, days for a repeat analysis with the appropriate crossover treatment. Subjects were randomized in equal numbers to study sequences using computer-generated random assignments.

Subjects who met the eligibility criteria were instructed to consume a high carbohydrate diet (more than 150 g of carbohydrate per day) on each of the three days before each test. Food intake was recorded in diet diaries by each subject to estimate carbohydrate consumption. On the evening before the meal glucose tolerance test, subjects consumed a low-residue dinner consisting of one 8 fl oz (237 ml) can of chocolate Ensure Plus® with additional Ensure® Nutrition and Energy Bars to provide about one-third of each subjects individual daily caloric requirement as estimated by the Harris-Benedict equation (Harris and Benedict, 1919) multiplied by an activity factor of 1.3. Subjects fasted overnight (10 to 16 hours) prior to test. During fasting, subjects were only allowed to consume water. Smoking was prohibited. Subjects did not exercise for the 24 hour period prior to the meal glucose tolerance test.

The morning following an overnight fast, subjects came to the testing laboratory and relaxed for at least 30 minutes prior to a baseline blood sample collection. Subjects then consumed the appropriate test product within a 10-minute time period and additional blood samples were taken at 15, 30, 45, 60, 90, 120, 150 and 180 minutes postprandial within ±5 minutes at each time point. The subjects recorded medications and subjective gastrointestinal tolerance data over the next 48 hours after the test.

2.1.1 Collection of Biological Samples

After the overnight fast (10–16 hour fast) and at least 30 minutes of rest at the clinical site, blood was obtained by finger-prick (self-administered unless subject requests otherwise; using a sterile lancing device) immediately prior to the meal glucose tolerance test. Multiple blood samples were obtained during the meal glucose tolerance test via self-administered finger-prick. A finger-prick sample was repeated if blood collection was insufficient and milking of the sample site was avoided to prevent the introduction of excess tissue fluid into the sample. Capillary blood glucose was measured using a YSI analyzer (model YSI 2700 Select Biochemistry Analyzer, Yellow Springs Instruments, Yellow Springs, Ohio). Incremental area under the glucose curve was calculated according to Wolever et al. (1991).

2.1.2 Dietary Records

Dietary records were taken for the three consecutive days prior to the study visits. Subjects entered the amount and type of all foods and liquids ingested during this time period. The investigator or coordinator reviewed the dietary records with each subject upon completion of each set of 3-day dietary records to ensure that: 1) the most accurate estimate of serving sizes of each of the foods had been recorded, and 2) there was sufficient information recorded to estimate the daily amount of carbohydrate intake for the three day period (>150 grams needed daily).

2.1.4 Study Product Intake

Subjects were given commercial Ensure® products for the evening meals preceding Visit 1 and Visit 2 at the prior visit. The subjects were asked about compliance for these evening meals, which was recorded on a case report form. At Visit 1 and Visit 2 the study staff witnessed study product intake for each subject during the meal glucose tolerance test. Subjects ingested the study product in its entirety within a 10-minute period, and compliance was recorded on a case report form.

2.2 Selection of Study Population

Subjects were recruited from various populations, including previous study subjects and other individuals from the general population. Subjects eligible for study participation were to satisfy the following criteria.

2.2.1 Inclusion Criteria

Eligibility criteria for study enrollment included:

1. Subject is 18–75 years of age.
2. Subject is male or non-pregnant female at least six weeks postpartum and no lactating.
3. Subject is not currently receiving oral contraceptives or oral hormone replacement therapy.
4. Subject has a body mass index (BMI) of 20–28 kg/m$^2$.
5. Subject does not have diabetes mellitus or glucose intolerance (screen capillary blood glucose <110 mg/dL).
6. Subject is free from active metabolic or gastrointestinal diseases that may interfere with nutrient absorption, distribution, metabolism, or excretion and has no known food allergies.
7. Subject has not had an infection (requiring medication or hospitalization), surgery, or corticosteroid treatment in the last 3 months or antibiotics in the last 3 weeks.
8. Subject is not taking daily medications (e.g., acetaminophen, salicylates, diuretics, etc.) that would interfere with nutrient absorption, metabolism, excretion or gastric motility.
9. Subject does not smoke.
10. Subject has voluntarily signed and personally dated an informed consent form prior to any participation in the study.

2.3.1 Primary Variable

The primary variable was baseline-adjusted peak blood glucose concentration.

2.4 Treatments 2.4.1 Treatments Administered

Upon fulfilling the entrance criteria and receiving consent of the subject or subject's legally acceptable representative prior to any study participation, treatment assignments were carried out by using a prospectively generated randomization plan. Subjects received both study products, in a randomized order. Subjects must have consumed at least 150 g carbohydrate per day for the 3 days prior to, consumed their low residue meal the evening prior to, refrained from exercise for the 24 hour period prior to, and fasted for 10 to 16 hours prior to the meal glucose tolerance test. If subject fails to adhere to these guidelines prior to the test, he/she returned for another study date. The study staff were responsible for allotting and dispensing of the study product.

2.4.2 Identity of Investigational Product(s)

Subjects received both products in a randomized order. The two treatments evaluated in this experiment were: 1) maltodextrin and 2) pullulan. Maltodextrin is a partially hydrolyzed cornstarch that is a common ingredient in many processed foods and is generally recognized as safe (GRAS; 21 CFR 184.1444). Pullulan is a starch-like food ingredient that has been used as a dietary gum, serving as a texturizer for tofu, ham and sausage, as a substrate for flavors and as a means of protecting flavors through micro encapsulation, and as a food film (Kimoto et al., 1997). These carbohydrates were incorporated into juice-like beverages (~25 g per 250 ml) and flavored to enhance palatability. A detailed description of the nutritional profiles of the products can be found in Appendix A.

2.4.3 Selection and Timing of Levels of Test Product for Each Subject

The study consisted of two treatment days (Visit 1 and Visit 2) with a minimum washout period of four days in between and optimally a maximum of 14 days between study visits. For each meal glucose tolerance test, subjects consumed 2 servings (~8 fl oz/serving) of study product that provided 50 g of carbohydrate. The study products were consumed at a similar time each day during each treatment visit.

2.4.4 Blinding

This was a double-blind study. Products were labeled with a clinical product number and the code for product identification was kept by sponsor, Abbott Laboratories.

2.5.5 Treatment Compliance

Treatment compliance was measured by tracking whether study product was dispensed to subjects during each of their visits at the study site and by witnessing the subject consume the product in its entirety (within 10 minutes).

3.0 Statistical Methods 3.1 Statistical and Analytical Plans

This was a randomized, double-blind, two-period, two-treatment, crossover study conducted at a single site. At least 26 subjects (13 in each treatment sequence) were randomized to obtain a complete set (period 1 and 2) of values for the primary variable for 26 subjects. The statistical analyses and summaries were performed on the evaluable subject data and intent to treat (secondary data: all randomized subjects) data. Missing data were not imputed and a subject having missing data for a variable at one or more periods was not included in the analysis for that variable. There was no interim analyses.

The following two steps were carried out for each two-period crossover analysis:

1. Test for sequence effect:
   a. Compare two treatment sequences for the values, sum of two periods, using two-sided t-test or (if non-normal two-sided Wilcoxon Rank Sum test.
2. Test for treatment effect:
   a. If the sequence effect is not significant (p≧0.10) then compare two treatment sequences for the values, difference of two periods, by two-sided t-test or (if non-normal) two-sided Wilcoxon Rank Sum test.
   b. If the sequence effect is significant (p<0.10) then compare two treatments using only the first period data by two-sided t-test or (if non-normal) two-sided Wilcoxon Rank Sum test.

A result (except for sequence effect) was declared to be statistically significant if and only if a p-value of an analysis is less than 0.05.

Primary Variable

Change from baseline (0 minute) for peak glucose concentration was analyzed using two-period crossover analysis.

Secondary Variable

The following variables were analyzed using two-period crossover analysis:

Area under the glucose curve (0–180 minutes) above the horizontal line at the zero minute value.

Baseline (0 minute) and change from baseline for blood glucose concentrations at individual time points (15, 30, 45, 60, 90, 120, 150, and 180 minutes ±5 minutes postprandial).

3.2 Determination of Sample Size

A sample size of 26 (13 in each treatment sequence) subjects had 80% power to detect a 15% difference in means for change from baseline (0 minute) for peak glucose concentration using a two group t-test with a 0.05 two-sided significance level (nQuery Advisor® Release 4.0). The t-test compares two treatment sequences for the primary variable, change from baseline (0 minute) for peak glucose concentration, using period 2–period 1 values.

The following were assumed for the estimation:
1. Mean change from baseline (0 minute) for peak glucose concentration for a treatment group is 4.095 μmol per liter (from EN-9819).
2. Standard deviation of change from baseline (0 minute) for peak glucose concentration (period 2–period 1) is 1.053 μmol per liter (from EN-9823 to EN-9819 sequence).

Results

Figure 3:
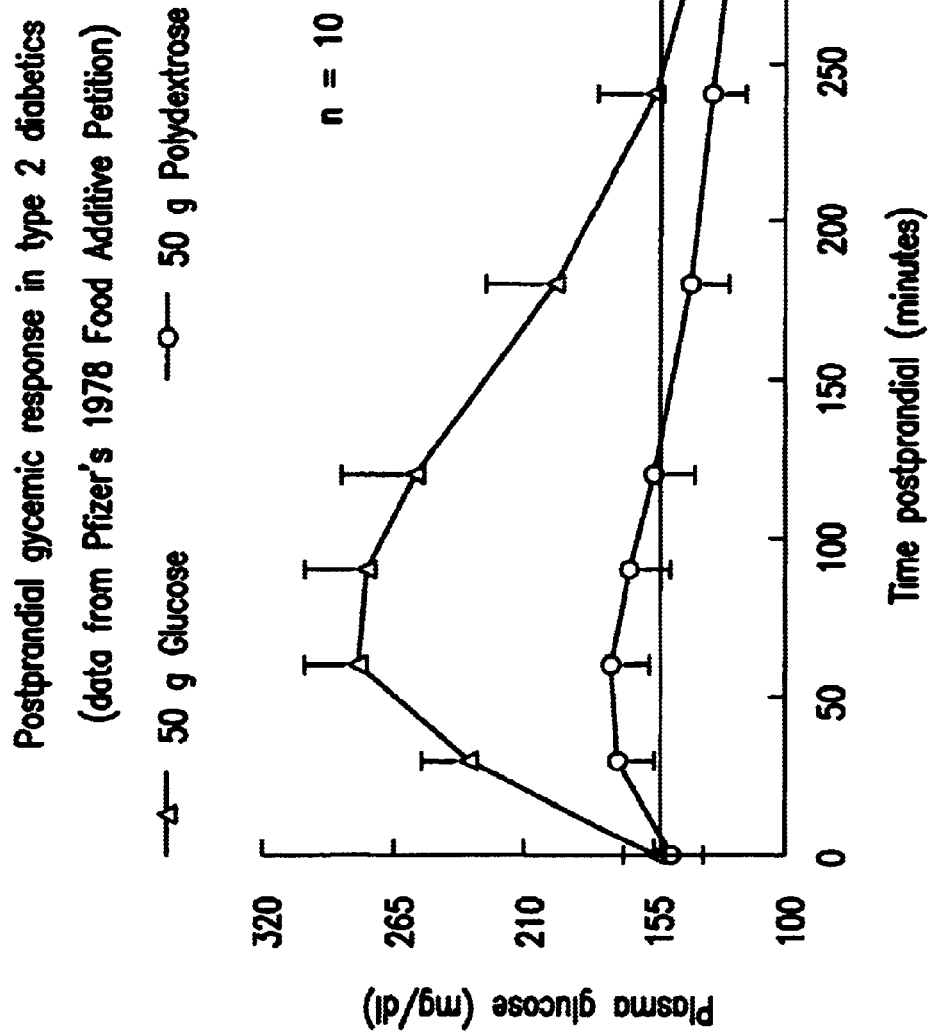
FIG. 3 is presented for comparative purposes. It discloses data published by Pfizer Inc., Polydextrose food additive petition. New York: Pfizer Inc., 1978 (FDA petition (A3441). It compares the glycemic response produced by glucose and the indigestible polysaccharide, polydextrose in maturity—onset diabetic subjects. As depicted in FIG. 3, the indigestible carbohydrate had essentially no effect on the subjects blood glucose levels (i.e., the compound was not converted to glucose).
Figure 4:
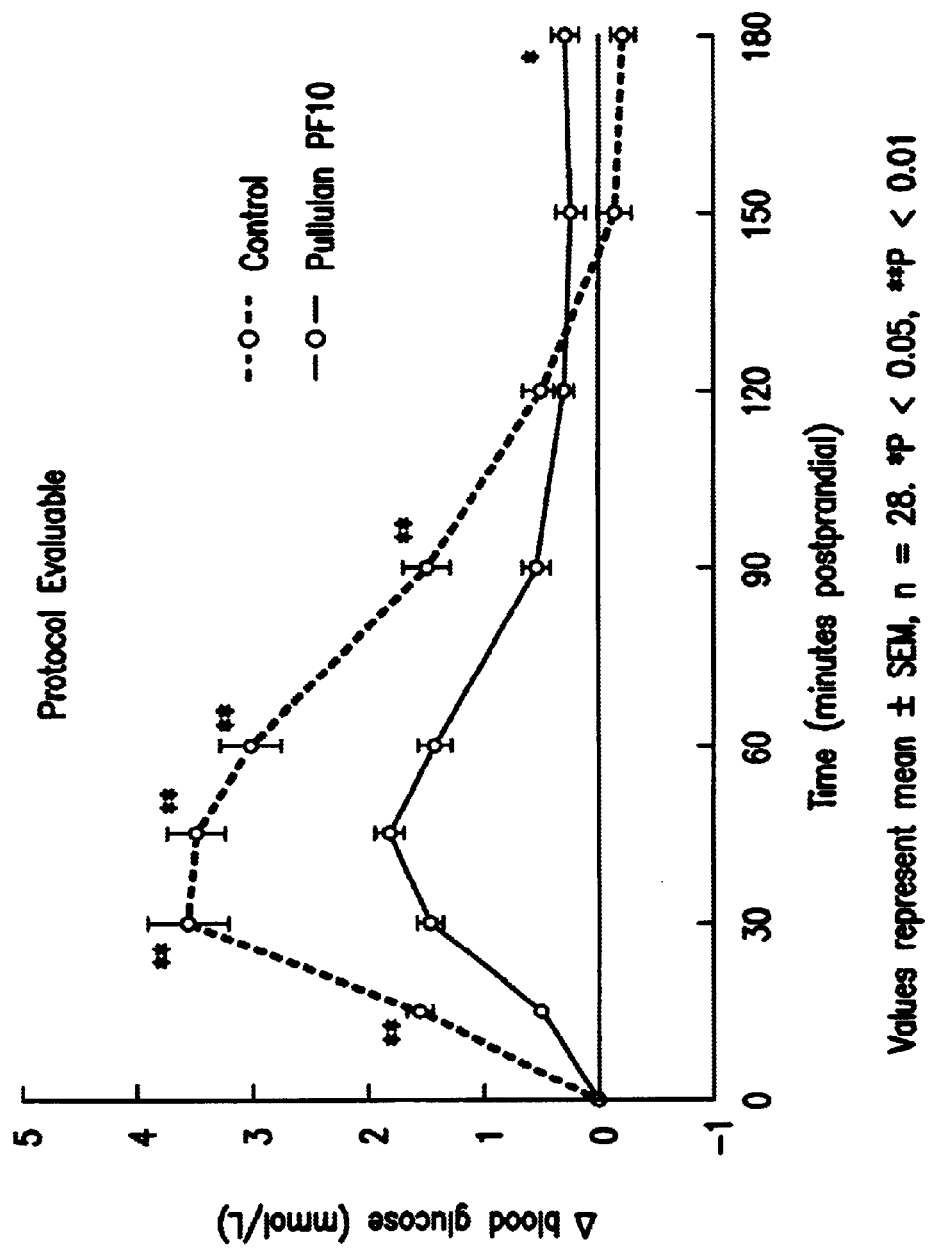
FIG. 4 presents the glycemic response of human subjects fed maltodextrin and pullulan as described in Example V.

The postprandial glycemic response of healthy subjects fed maltodextrin (control) or pullulan can be found in FIG. 4. Pullulan caused a rise in blood glucose above baseline (fasting) levels over the 3 hour postprandail period. If pullulan was resistant to digestion, as classified by the prior art, one would not expect a posprandial rise in blood glucose. As an example, FIG. 3, shows the minimal changes in postprandial blood glucose concentrations of diabetic subjects fed the indigestible polysaccharide, polydextrose.

Pullulan was digested slowly over the 3 hour meal glucose tolerance test as indicated by a reduced early phase excursion and then a maintenance of the later phase excursion compared with malodextrin, a rapidly digested starch. Incremental area under the glucose curve was lower (P<0.01) for subjects fed pullulan (268±15.6 vs. 135±11.6 mmol. min/L, maltodextrin and pullulan, respectively).

5.0 Reference List

American Diabetes Association. Report of the expert committee on the diagnosis and classification of diabetes mellitus (Committee Report). *Diabetes Care* 1998, 21, S5–S19.

American Diabetes Association. Nutrition recommendations and principles for people with diabetes mellitus (Position Statement). *Diabetes Care* 2001, 24 (Suppl. 1), S44–S47.

Berne, R. M.; Levy, M. N. Physiology. 4th Edition. St. Louis: Mosby 1998, 551.

Bond, J. H.; Levitt, M. D. Quantitative measurement of lactose absorption. *Gastroenterology* 1976, 70, 1058–1062.

Diabetes Control and Complications Trial (DCCT) Research Group. The effect of intensive treatment of diabetes on the development and progression of long-term complications in insulin-dependent diabetes mellitus. *New Engl. J. Med.* 1993, 329, 977–986.

Franz, M. J.; Coulston, A. M.; Horton, E. S.; Henry, R. R.; Bantle, J. P.; Hoogwerf, B. J.; Beebe, C. A.; Stacpoole, P. W.; Brunzell, J. D. Nutriton principles for the management of diabetes and related complications. *Diabetes Care* 1994, 17, 490–518.

Harris, J. A.; Benedict, F. G. *A biometric study of basal metaboism in man*; Carnegie Institute: Washington, D.C, p. 227 (Publ. No. 279), 1919.

Hertzler, S. R.; Huynh, B.-C. L.; Savaiano, D. A. How much lactose is low lactose? *J. Am. Diet. Assoc.* 1996, 96, 243–246. Hertzler, S., et al. How much lactose is low lactose? J Am Diet Assoc. 1996; 96: 243–246.

Jenkins, D. J. A.; Wolever, T. M. S.; Taylor, R. H.; Barker, H.; Fielden, H.; Baldwin, J. M.; Bowling, A. C.; Newman, H. C.; Jenkins, A. L.; Goff, D. V. Glycemic index of foods: a physiological basis for carbohydrate exchange. *Am. J. Clin. Nutr.* 1981, 34, 362–366.

Jenkins, D. J. A; Wolever, T. M. S.; Jenkins, A. L.; Thome, M. J.; Lee, R.; Kalmusky, J.; Reichert, R.; Wong, G. S. The glycemic index of foods tested in diabetic patients: a new basis for carbohydrate exchange favouring the use of legumes. *Diabetologia* 1983, 24, 257–264.

Keene, A. M. 1997. Physical examination. Ch. 12, in Black, J. M., and E. Matassarin-Jacobs. 1997. Medical-Surgical Nursing: Clinical Management for Continuity of Care, 5th ed. W. B. Saunders Co., Philadelphia, pp 213–241.

Kimoto, T.; Shibuya, T.; Shiobara, S. Safety studies of a novel starch, pullulan: chronic toxicity in rats and bacterial mutagenicity. *Food and Chemical Toxicology* 1997, 35, 323–329.

Klimt, C. R.; Prout, T. E.; Bradley, R. F.; Dolger, H.; Fisher, G.; Gastineau, C. F.; Marks, H.; Meinert, C. L.; Schumacher, O. P.; Cooper, G. R.; Mather, A.; Hainline, A.; Andres, R. Standardization of the oral glucose tolerance test: report of the committee on statistics of the American Diabetes Association. *Diabetes* 1969, 18, 299–307.

Krauss, R. M.; Eckel, R. H.; Howard, B.; Appel, L. J.; Daniels, S. R.; Deckelbaum, R. J.; Erdman Jr., J. W.; Kris-Etherton, P.; Goldberg, I. J.; Kotchen, T. A.; Lichtenstein, A. H.; Mitch, W. E.; Mullis, R.; Robinson, K; Wylie-Rosett, J.; St. Jeor, S.; Suttie, J.; Tribble, D. L.; Bazzarre, T. L. AHA Scientific Statement: AHA Dietary Guidelines: Revision 2000: A statement for healthcare professionals from the Nutrition Committee of the American Heart Association. *J. Nutr.* 2001, 131, 132–146.

Read, N. W.; Al-Janabi, M. N.; Bates, T. E.; Holgate, A. M.; Cann, P. A.; Kinsman, R. I.; McFarlane, A; Brown, C. Interpretation of the breath hydrogen profile obtained after ingesting a solid meal containing unabsorbable carbohydrate. *Gut.* 1985, 26, 834–842.

Strocchi, A.; Corazza, G.; Ellis, C. J.; Gasbarrini, G.; Levitt, M. D. Detection of malabsorption of low doses of carbohydrate: accuracy of various breath $H_2$ criteria. *Gastroenterology* 1993, 105, 1404–1410.

UK Prospective Diabetes Study (UKPDS) Group. Intensive blood-glucose control with sulphonylureas or insulin compared with conventional treatment and risk of complications in patients with type 2 diabetes (UKPDS 33). *Lancet* 1998, 352, 837–853.

Wolever, T. M. S.; Jenkins, D. J. A; Jenkins, A. L.; Josse, R. G. The glycemic index: methodology and clinical implications. *Amer. J. Clin. Nutr.* 1991, 54, 846–854.

Wolf, B. W. Discovery of a carbohydrate system that does not exacerbate postprandial glycemia. Ph.D. Dissertation. The Ohio State University, Columbus. 2001.

APPENDIX A

Additional Study Supplies and Information provided to Study Site

| | Control | Test |
|---|---|---|
| | units per 8 fl oz serving | |
| Composition of Study Products | | |
| Maltodextrin, g | 25 | 0 |
| Pullulan, g | 0 | 25 |
| Sodium, mg | 27 | 27 |
| Potassium, mg | 47 | 47 |
| Chloride, mg | 42 | 42 |

APPENDIX A-continued

Additional Study Supplies and Information provided to Study Site

|  | Control | Test |
|---|---|---|
| Vitamin C, mg | 60 | 60 |

Subjects consumed 2–8 fl oz servings of product at each meal glucose tolerance test that provided a total of 50 g of carbohydrate.

| Ingredient Listings | units per batch | |
|---|---|---|
| Sodium chloride, g | 200 | 200 |
| Potassium citrate, g | 400 | 400 |
| Sodium citrate, g | 10 | 10 |
| Ascorbic acid, g | 1000 | 1000 |
| Pullulan PF-10, lb | 0 | 65 |
| Maltrin M 100, lb | 65 | 0 |
| Water, lb | 540 | 540 |
| Artificial wildberry, lb | 1.2 | 1.2 |
| Natural cinnamon, g | 110 | 110 |
| FD&C Red #3, g | 52 | 52 |
| FD&C Blue #1, g | 3 | 3 |
| Sucralose powder, g | 68 | 68 |

We claim:

1. A meal replacement product comprising:
   a) a protein source;
   b) a fat source, and;
   c) a carbohydrate system, which includes at least one slowly digesting carbohydrate selected from the group consisting of pullulan, in which said pullulan is present in the quantity of at least 5 w/w %, based upon the total carbohydrate present, when measured on a dry weight basis.

2. The meal replacement product according to claim 1 in which said product contains:
   a) a protein source providing from about 10 to about 35% of total calories
   b) a fat source providing from about 10 to about 50% of total calories, and;
   c) a carbohydrate system providing from about 25 to about 80% of total calories.

3. An article of manufacture comprising the packaged meal replacement product according to claim 1, in which said article bears a label indicating the contents should be consumed by a diabetic.

4. An article of manufacture comprising the packaged meal replacement product according to claim 1, in which said article bears a label indicating the contents should be consumed by a human attempting to loose weight.

5. A method of producing a blunted glycemic response in a diabetic patient comprising administering to said diabetic patient a meal replacement product, said meal replacement product contains:
   a) a protein source
   b) a fat source and;
   c) a carbohydrate system, in which said pullulan is present in the quantity of at least 5 w/w %, based upon the total carbohydrate present, when measured on a dry weight basis.

6. The method according to claim 5 in which said meal replacement product is a bar or a beverage.

7. The method according to claim 5 in which said meal replacement product contains:
   a) a protein source providing from about 10 to about 35% of total calories
   b) a fat source providing from about 10 to about 50% of total calories, and;
   c) a carbohydrate system providing from about 25 to about 80% of total calories.

8. A method for providing nutrition to a diabetic patient comprising feeding to said diabetic patient a meal replacement product, said meal replacement product contains:
   a) a protein source
   b) a fat source and;
   c) a carbohydrate system, in which said pullulan is present in the quantity of at least 5 w/w %, based upon the total carbohydrate present, when measured on a dry weight basis.

9. The method according to claim 8 in which said meal replacement product is a bar or a beverage.

10. The method according to claim 8 in which said meal replacement product contains:
    a) a protein source providing from about 10 to about 35% of total calories
    b) a fat source providing from about 10 to about 50% of total calories, and;
    c) a carbohydrate system providing from about 25 to about 80% of total calories.

11. A method for assisting a diabetic patient with managing their blood glucose levels comprising feeding said patient a meal replacement product, said meal replacement product contains:
    a) a protein source
    b) a fat source and;
    c) a carbohydrate system, in which said pullulan is present in the quantity of at least 5 w/w %, based upon the total carbohydrate present, when measured on a dry weight basis.

12. A method for providing for the prolonged release of glucose comprising administering to a diabetic patient in need thereof a meal replacement product, said meal replacement product contains:
    a) a protein source
    b) a fat source and;
    c) a carbohydrate system, in which said pullulan is present in the quantity of at least 5 w/w %, based upon the total carbohydrate present, when measured on a dry weight basis.

13. A method for producing satiety in a human comprising feeding said human a meal replacement product, said meal replacement product contains:
    a) a protein source
    b) a fat source and;
    c) a carbohydrate system, in which said pullulan is present in the quantity of at least 5 w/w %, based upon the total carbohydrate present, when measured on a dry weight basis.

14. A method for assisting a human in a weight loss program comprising feeding said human a meal replacement product, said meal replacement product contains:
    a) a protein source
    b) a fat source and;
    c) a carbohydrate system, in which said pullulan is present in the quantity of at least 5 w/w %, based upon the total carbohydrate present, when measured on a dry weight basis.

15. A method for promoting weight loss in a human comprising feeding to said human a meal replacement product, said meal replacement product contains:
    a) a protein source
    b) a fat source and;
    c) a carbohydrate system, in which said pullulan is present in the quantity of at least 5 w/w %, based upon the total carbohydrate present, when measured on a dry weight basis.

16. The method according to claim 15 in which said meal replacement product is a bar or a beverage.

17. The method according to claim 15 in which said meal replacement product contains:
   a) a protein source providing from about 10 to about 35% of total calories
   b) a fat source providing from about 10 to about 50% of total calories, and;
   c) a carbohydrate system providing from about 25 to about 80% of total calories.

18. A method for preventing hypoglycemia in a diabetic comprising administering to said diabetic a meal replacement product, said meal replacement product contains:
   a) a protein source
   b) a fat source and;
   c) a carbohydrate system, in which said pullulan is present in the quantity of at least 5 w/w %, based upon the total carbohydrate present, when measured on a dry weight basis.

* * * * *